United States Patent
Takahashi

(10) Patent No.: US 10,123,744 B2
(45) Date of Patent: Nov. 13, 2018

(54) BIOSENSOR

(71) Applicant: Murata Manufacturing Co., Ltd., Nagaokakyo-shi, Kyoto-fu (JP)

(72) Inventor: Eiji Takahashi, Nagaokakyo (JP)

(73) Assignee: MURATA MANUFACTURING CO., LTD., Nagaokakyo-shi, Kyoto-fu (JP)

(*) Notice: Subject to any disclaimer, the term of this patent is extended or adjusted under 35 U.S.C. 154(b) by 71 days.

(21) Appl. No.: 14/953,795

(22) Filed: Nov. 30, 2015

(65) Prior Publication Data

US 2016/0081626 A1    Mar. 24, 2016

Related U.S. Application Data

(63) Continuation of application No. PCT/JP2014/063554, filed on May 22, 2014.

(30) Foreign Application Priority Data

May 30, 2013 (JP) .................................. 2013-113547

(51) Int. Cl.
*A61B 5/00* (2006.01)
*A61B 5/024* (2006.01)
*A61B 5/1455* (2006.01)

(52) U.S. Cl.
CPC ........ *A61B 5/7203* (2013.01); *A61B 5/02427* (2013.01); *A61B 5/7225* (2013.01); *A61B 5/14551* (2013.01)

(58) Field of Classification Search
CPC . A61B 5/7203; A61B 5/02427; A61B 5/7225; A61B 5/14551

(Continued)

(56) References Cited

U.S. PATENT DOCUMENTS 4,863,265 A * 9/1989 Flower ............... A61B 5/14551
356/41
4,867,571 A * 9/1989 Frick .................. A61B 5/02416
356/41

(Continued)

FOREIGN PATENT DOCUMENTS

CN    102028457 A    4/2011
JP    2008-188216 A    8/2008

(Continued)

OTHER PUBLICATIONS

International Search Report issued for PCT/JP2014/063554, dated Aug. 12, 2014.

(Continued)

*Primary Examiner* — Catherine Voorhees
*Assistant Examiner* — Roland Dinga
(74) *Attorney, Agent, or Firm* — Arent Fox LLP

(57) ABSTRACT

There is provided a biosensor capable of improving the S/N ratio of a final photoplethysmographic signal regardless of the change in a noise component such as extraneous light. A biosensor includes a driving signal generation unit for generating a pulsed driving signal, a light-emitting element for emitting light in response to a generated driving signal, a light-receiving section including a light-receiving element for outputting a detection signal in accordance with the intensity of light received and an amplification unit for amplifying a detection signal output from the light-receiving element, a filter unit for removing a pulse wave component from a detection signal output from the light-receiving section to obtain a baseline signal, and a differential amplification unit for taking a difference between a detection signal output from the light-receiving section and a baseline signal obtained by the filter unit.

17 Claims, 12 Drawing Sheets

(58) Field of Classification Search
USPC .................................. 600/301, 336, 509, 513
See application file for complete search history.

(56) References Cited

U.S. PATENT DOCUMENTS

| | | | |
|---|---|---|---|
| 8,478,538 B2 | 7/2013 | McGonigle et al. | |
| 2003/0083584 A1* | 5/2003 | Yonce .................. | A61B 5/0424 600/509 |
| 2010/0286495 A1 | 11/2010 | McGonigle et al. | |
| 2011/0237965 A1 | 9/2011 | Hayashi et al. | |
| 2012/0071734 A1* | 3/2012 | Shimuta ............... | A61B 5/0205 600/301 |
| 2012/0220881 A1 | 8/2012 | Takahashi | |

FOREIGN PATENT DOCUMENTS

| | | |
|---|---|---|
| JP | 2009-066119 A | 4/2009 |
| JP | 2009-201801 A | 9/2009 |
| JP | 2010-166963 A | 8/2010 |
| JP | 2011-200271 A | 10/2011 |
| JP | 2012-178196 A | 9/2012 |

OTHER PUBLICATIONS

Written Opinion of the International Searching Authority issued for PCT/JP2014/063554, dated Aug. 12, 2014.

* cited by examiner

BIOSENSOR

CROSS REFERENCE TO RELATED APPLICATION

The present application is a continuation of PCT/JP2014/063554 filed May 22, 2014, which claims priority to Japanese Patent Application No. 2013-113547, filed May 30, 2013, the entire contents of each of which are incorporated herein by reference.

FIELD OF THE INVENTION

The present invention relates to a biosensor for detecting biological information.

BACKGROUND OF THE INVENTION

Photoplethysmography meters and pulse oximeters are known. Using characteristics where hemoglobin in the blood absorbs light in a range from visible light to infrared light, such a meter obtains a change in the intensity of light that is emitted from a light-emitting diode (light-emitting element), passes through or is reflected by a living body such as a finger, and enters a photodiode (light-receiving element) as a photoplethysmographic signal (see, for example, Patent Documents 1 and 2). Extraneous light (for example, sunlight or fluorescent light) other than light emitted from the light-emitting diode sometimes enters the photodiode. Light emitted from the light-emitting diode sometimes enters the photodiode without passing through the living body or being reflected by the living body (stray light). The extraneous light and the stray light are superimposed on, light required to be detected, that is, light that has passed through the living body or been reflected by the living body, and the signal-to-noise (S/N) ratio of a detection signal may be reduced.

Patent Document 1 discloses a pulse oximeter that improves the S/N ratio of a detection signal by performing the subtraction of a reference voltage whose level corresponds to a non-fluctuating (DC) component excluding a pulsating component (pulse wave component). This pulse oximeter includes a first light source (light-emitting element), a second light source (light-emitting element), and a photodiode (light-receiving element).

The light-receiving output (current signal) of the photodiode is converted into a voltage signal on the basis of a reference voltage (Vref 1) by a current/voltage conversion circuit and is amplified by an amplification circuit (amplifier). The amplified voltage signal is converted into a digital signal by an analog-to-digital (A/D) conversion circuit and is input into a computation device. The computation device calculates a reference voltage whose level corresponds to a non-fluctuating (DC) component excluding a pulsating component (pulse wave component) on the basis of the above-described digital signal. The reference voltage is supplied to the current/voltage conversion circuit and is subtracted from a current signal that is a light-receiving output. As a result, a voltage signal corresponding to a pulsating component is output as a detection signal.

Patent Document 2 discloses a pulse wave amplification apparatus that changes a reference voltage for an amplification circuit in consideration of the change in a noise component. This pulse wave amplification apparatus includes a pulse wave detection sensor having a light-emitting element and a light-receiving element, a pulsation pulse generation circuit for generating a pulsation pulse, a conversion circuit for converting the output of the pulse wave detection sensor into an analog signal, an amplification circuit for sampling and holding the analog signal in synchronization with the pulsation pulse, setting a value obtained by the sampling and the holding as a reference voltage, and amplifying a pulse wave signal included in the analog signal using the reference voltage, and a DC store circuit for restoring the DC level of the pulse wave signal output from the amplification circuit in synchronization with the pulsation pulse.

Patent Document 1: Japanese Unexamined Patent Application Publication No. 2009-66119.

Patent Document 2: Japanese Unexamined Patent Application Publication No. 2010-166963.

The pulse oximeter disclosed in Patent Document 1 can improve the S/N ratio of a detection signal by performing the subtraction of the reference voltage under conditions where a noise component does not vary even in a case where light on which extraneous light, stray light, or the like is superimposed enters the light-receiving element. However, in a case where a noise component varies in accordance with the change in extraneous light or the change in stray light caused by the movement of a human body, it is difficult for the pulse oximeter disclosed in Patent Document 1 to remove the varying noise component. Accordingly, in a case where a noise component such as extraneous light varies, the S/N ratio of a photoplethysmographic signal may be reduced.

The pulse wave amplification apparatus disclosed in Patent Document 2 can set a reference voltage for each pulsation pulse in accordance with the change in noise component and amplify a pulse wave signal. However, in a case where a noise component varies in the middle of one pulsation pulse cycle, it is impossible to respond to the change in a noise component. Accordingly, in a case where a noise component such as extraneous light varies, the S/N ratio of a photoplethysmographic signal may be reduced.

SUMMARY OF THE INVENTION

It is an object of the present invention to provide a biosensor capable of improving the S/N ratio of a final photoplethysmographic signal even when a noise component such as extraneous light varies.

A biosensor according to the present invention includes a driving signal generation unit configured to generate a driving signal, a light-emitting element configured to emit light in response to a driving signal generated by the driving signal generation unit, a light-receiving element configured to output a detection signal in accordance with an intensity of light received, a baseline signal acquisition unit or filter configured to remove a pulse wave component from a detection signal output from the light-receiving element to acquire a baseline signal, and a difference acquisition unit configured to take a difference between the detection signal and the baseline signal acquired by the baseline signal acquisition unit.

In a biosensor according to the present invention, a pulse wave component is removed from a detection signal and a remaining noise component is obtained as a baseline signal. Accordingly, the baseline signal varies in accordance with the change in a noise component superimposed on a detection signal which is caused by, for example, the movement of a human body or the change in extraneous light. By taking a difference between the detection signal and the baseline signal, the noise component can be cut and a photoplethysmographic signal (pulse wave component) included in the detection signal can be detected. Accordingly, the S/N ratio of a final photoplethysmographic signal can be improved regardless of the change in a noise component such as extraneous light.

The biosensor according to the present invention preferably further includes an envelope extraction unit configured to extract an envelope of a detection signal output from the light-receiving element. The driving signal generation unit preferably generates a pulsed driving signal. The baseline signal acquisition unit or filter preferably removes a pulse wave component from the envelope of the detection signal extracted by the envelope extraction unit to acquire a baseline signal.

In this case, the light-emitting element flashes in response to a pulsed driving signal. As compared with a case where the light-emitting element is kept lighted, power consumption can be reduced. By extracting the envelope of a pulsed detection signal output from the light-receiving element, the pulsed detection signal is converted into a signal with a continuous waveform representing the envelope. By removing a pulse wave component from the envelope of the detection signal, a baseline signal with a continuous waveform is obtained. That is, the baseline signal with a continuous waveform corresponds to a noise component obtained by the removal of the pulse wave component. The baseline signal therefore varies in accordance with the change in the noise component. By taking a difference between the pulsed detection signal and the baseline signal, the noise component can be cut and a pulsed photoplethysmographic signal (pulse wave component) included in the detection signal can be obtained.

A biosensor according to the present invention includes a driving signal generation unit configured to generate a pulsed driving signal, a light-emitting element configured to emit light in response to a driving signal generated by the driving signal generation unit, a light-receiving element configured to output a detection signal in accordance with an intensity of light received, an envelope extraction unit configured to extract an envelope of a detection signal output from the light-receiving element, a baseline signal acquisition unit or filter configured to remove a pulse wave component from the envelope of the detection signal extracted by the envelope extraction unit to acquire a baseline signal, and a difference acquisition unit configured to take a difference between the envelope of the detection signal and the baseline signal acquired by the baseline signal acquisition unit.

In the biosensor according to the present invention, the light-emitting element flashes in response to the above-described pulsed driving signal. As compared with a case where the light-emitting element is kept lighted, power consumption can be reduced. By extracting the envelope of a pulsed detection signal, the pulsed detection signal is converted into a signal with a continuous waveform representing the envelope. By removing a pulse wave component from the envelope of the detection signal, a baseline signal with a continuous waveform is obtained. By taking a difference between the envelope of the detection signal with a continuous waveform and the baseline signal, a noise component can be cut and a photoplethysmographic signal (pulse wave component) with a continuous waveform included in the envelope of the detection signal can be obtained. Accordingly, the S/N ratio of a final photoplethysmographic signal can be improved regardless of the change in a noise component such as extraneous light.

The biosensor according to the present invention preferably further includes a high-pass filter configured to, among detection signals output from the light-receiving element, selectively pass detection signals of frequencies equal to or higher than a predetermined frequency which include the pulse wave component. The envelope extraction unit preferably extracts an envelope of a detection signal that has passed through the high-pass filter.

With the high-pass filter, among detection signals output from the light-receiving element, detection signals of frequencies equal to or higher than a predetermined frequency, which include the pulse wave component, can be selectively passed. That is, the high-pass filter removes a noise component that is less variable than a pulse wave component on a time axis. As a result, the S/N ratio of a detection signal can be improved and the amplification factor of an amplification circuit can be increased. The envelope of the detection signal that has passed through the high-pass filter is extracted, and a pulse wave component is removed from the envelope of the detection signal, so that a baseline signal is obtained. By taking a difference between the detection signal having the improved S/N ratio and the baseline signal having the improved S/N ratio, a noise component can be more accurately cut.

In the biosensor according to the present invention, the envelope extraction unit preferably includes an ideal diode circuit configured to equivalently eliminate a diode forward voltage drop, and the envelope extraction unit preferably rectifies a detection signal output from the light-receiving element using the ideal diode circuit and then removes a high-frequency component from the detection signal and then extracts an envelope of the detection signal.

When the detection of an envelope of a detection signal is performed with a commonly-used diode, the output of an envelope (the waveform of a pulse wave) is distorted under the influence of the nonlinearity of the diode. However, since the ideal diode circuit capable of equivalently eliminating a diode forward voltage drop is used, the nonlinearity of a commonly-used diode does not become a problem and the distortion of the output of an envelope (the distortion of the waveform of a pulse wave) can be prevented.

In the biosensor according to the present invention, the ideal diode circuit preferably includes an operational amplifier configured to receive a detection signal from the light-receiving element and a diode having an anode terminal connected to an output terminal of the operational amplifier and a cathode terminal connected to an output of the ideal diode circuit and a feedback loop of the operational amplifier.

By disposing the diode in the feedback loop of the operational amplifier, the nonlinearity and temperature characteristics of the diode can be compressed to a fraction of a loop gain (that is, can be improved). As a result, the above-described ideal diode circuit can be realized.

In the biosensor according to the present invention, the baseline signal acquisition unit is preferably a band elimination filter configured to, among the detection signals, selectively block passage of a detection signal in a frequency band including a pulse wave component to acquire a baseline signal.

With the band elimination filter, the passage of a detection signal in a frequency band including a pulse wave component is blocked to obtain a baseline signal. That is, the baseline signal corresponds to a noise component obtained by the removal of the pulse wave component. The baseline signal therefore varies in accordance with the change in the noise component. By taking a difference between the detection signal and the baseline signal, the noise component can be cut.

In the biosensor according to the present invention, the baseline signal acquisition unit is preferably a low-pass filter configured to, among the detection signals, selectively pass a detection signal of a frequency lower than frequencies including a pulse wave component to acquire a baseline signal.

With the low-pass filter, a detection signal of a frequency lower than frequencies including a pulse wave component is passed to obtain a baseline signal. That is, a detection signal of a frequency equal to or higher than frequencies including a pulse wave component is removed. Accordingly, the baseline signal corresponds to a noise component obtained by the removal of the pulse wave component. The baseline signal therefore varies in accordance with the change in the noise component. By taking a difference between the detection signal and the baseline signal, the noise component can be cut.

The biosensor according to the present invention preferably further includes an amplitude adjustment unit configured to adjust an amplitude of a signal input into the difference acquisition unit on the basis of an amplitude of a baseline signal acquired by the baseline signal acquisition unit.

Thus, on the basis of the amplitude of the baseline signal, the amplitude of a signal to be input into the difference acquisition unit can be adjusted. For example, in a case where the amplitude of the baseline signal is attenuated and becomes low, the amplitude of a detection signal output from the light-receiving element can be adjusted so that the detection signal has also a low amplitude. By taking a difference between the detection signal and the baseline signal, it is possible to efficiently cut a noise component and further improve the S/N ratio of a photoplethysmographic signal (pulse wave component).

According to the disclosed embodiments, the S/N ratio of a final photoplethysmographic signal can be improved even when a noise component such as extraneous light varies.

DETAILED DESCRIPTION OF THE EXEMPLARY EMBODIMENTS

Figure 1:
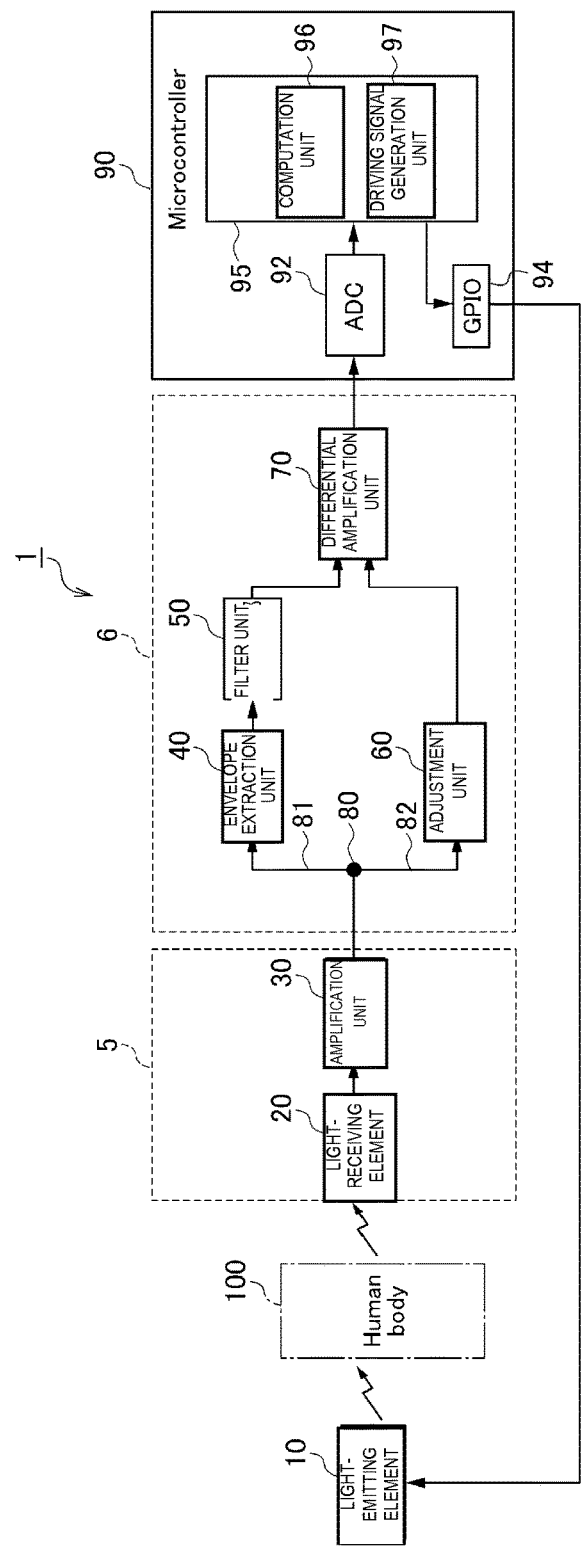
FIG. 1 is a block diagram illustrating the configuration of a biosensor according to a first embodiment.

Preferred embodiments of the present invention will be described in detail below with reference to the accompanying drawings. In the drawings, the same reference numeral is used to represent the same part or a corresponding part so as to avoid repeated explanation.

First Embodiment

Figure 2:
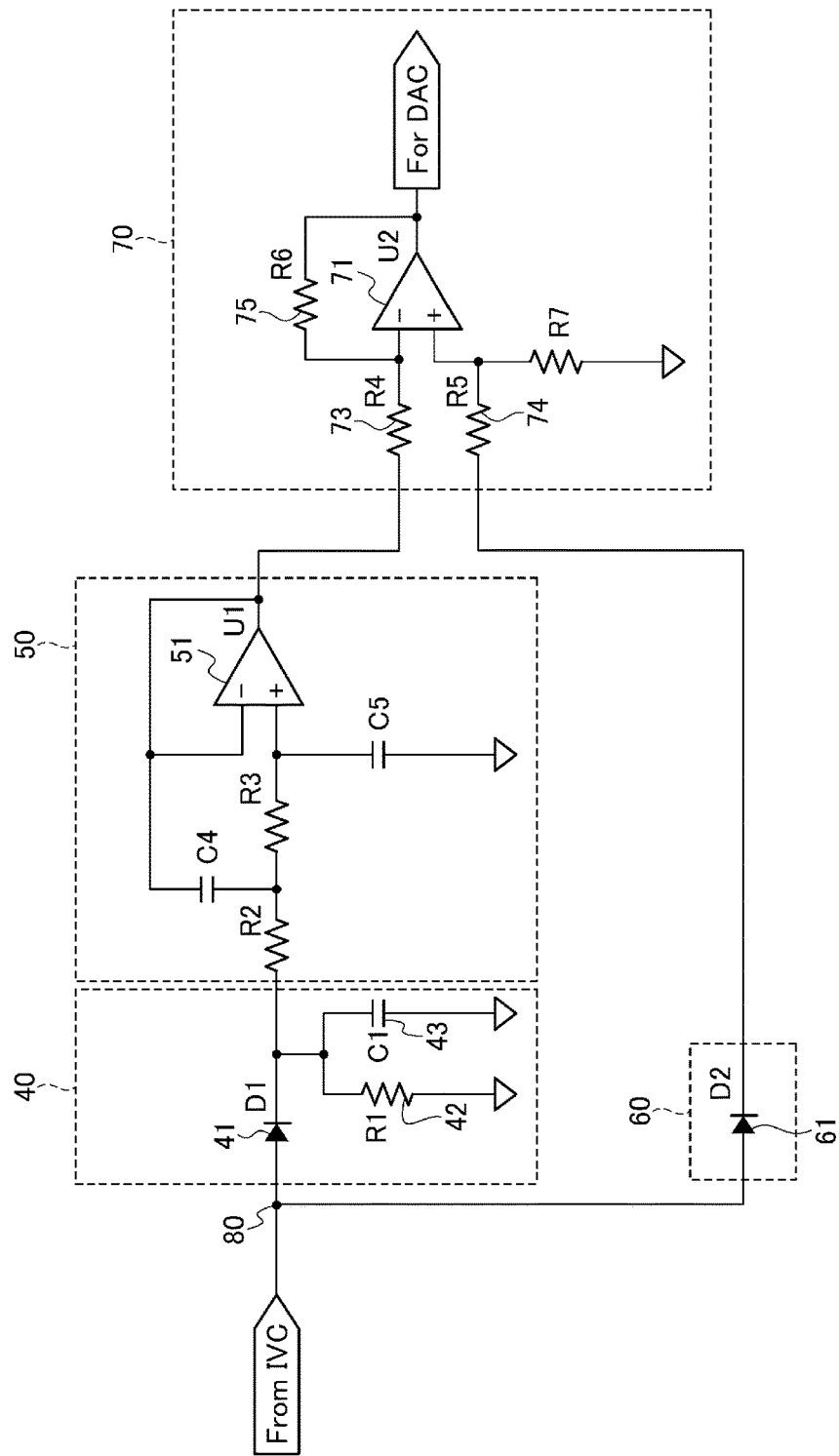
FIG. 2 is a circuit diagram of a pulse wave detection unit in a biosensor according to the first embodiment.
Figure 3:
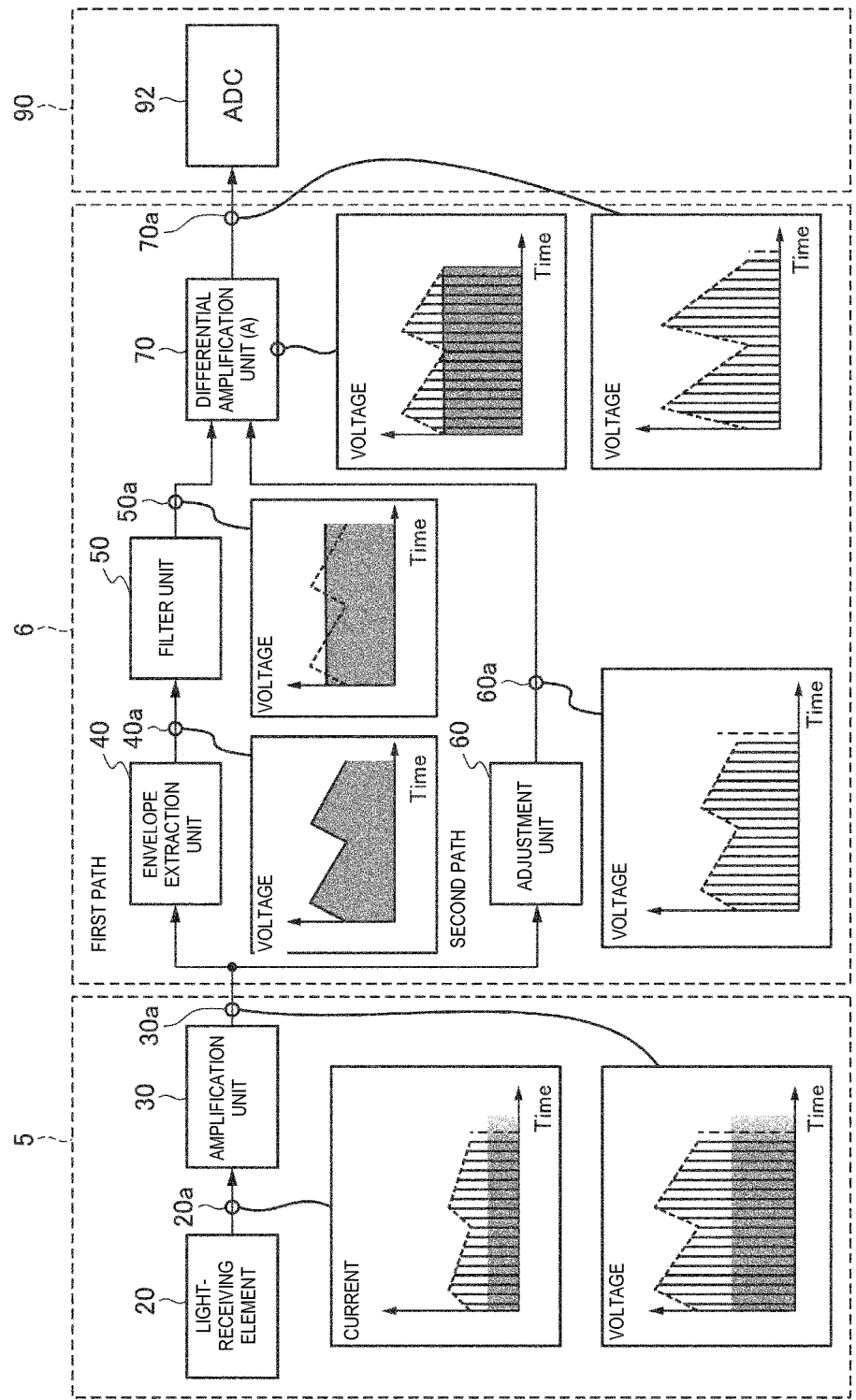
FIG. 3 is a diagram illustrating a signal waveform at each node in a biosensor according to the first embodiment.

First, the configuration of a biosensor 1 according to the first embodiment will be described with reference to FIGS. 1 to 3. FIG. 1 is a block diagram illustrating the configuration of the biosensor 1. FIG. 2 is a circuit diagram of a pulse wave detection circuitry 6 in the biosensor 1. FIG. 3 is a diagram illustrating a signal waveform at each node in the biosensor 1.

The biosensor 1 is, for example, a sensor that optically detects a photoplethysmographic signal and measures biological information such as pulse information using characteristics where hemoglobin in the blood absorbs light. The biosensor 1 includes a light-emitting element 10, a light-receiving section 5, the pulse wave detection circuitry 6, and a microcontroller 90. The light-receiving section 5 includes a light-receiving element 20 and an amplification unit 30. The pulse wave detection circuitry 6 includes an envelope extraction unit 40, a filter 50, an adjustment unit 60, and a differential amplification circuit 70.

The light-emitting element 10 emits light in response to a pulsed driving signal output from an output port 94 of the microcontroller 90. The light-emitting element 10 is, for example, a light-emitting diode (LED), a vertical cavity surface emitting laser (VCSEL), or a resonator-type LED.

The light-receiving element 20 outputs a detection signal in accordance with the intensity of light that has been emitted from the light-emitting element 10, passed through or been reflected by a human body 100 such as a fingertip, and entered the light-receiving element 20. The light-receiving element 20 is preferably, for example, a photodiode or a phototransistor. In this embodiment, a photodiode is used as the light-receiving element 20. The light-receiving element (photodiode) 20 is connected to the amplification unit 30, and outputs the detection signal (photoplethysmographic signal) (see an output waveform at a node 20a in FIG. 3) to the amplification unit 30.

The amplification unit 30 performs current/voltage conversion and amplification upon the detection signal (photoplethysmographic signal) (see the output waveform at the node 20a in FIG. 3) that is a current output of the light-receiving element (photodiode) 20. The amplification unit 30 therefore includes a current/voltage conversion circuit and an initial-stage amplification circuit. The output of the amplification unit 30 branches off into a first path 81 and a second path 82 at a branch point 80. The output terminal of the amplification unit 30 is connected to the anode terminal of a diode 41 forming the envelope extraction unit 40 on the first path 81, and is connected to the anode terminal of a diode 61 forming the adjustment unit 60 on the second path 82. The detection signal amplified by the amplification unit 30 is output to the envelope extraction unit 40 and the adjustment unit 60.

Figure 4:
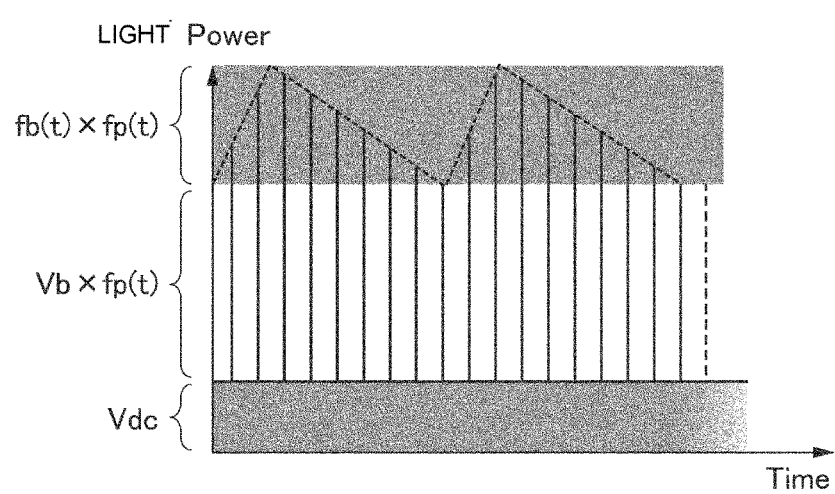
FIG. 4 is a diagram describing the component of a photoplethysmographic signal received by a light-receiving element in a biosensor.

The component of the detection signal (photoplethysmographic signal) output from the light-receiving element 20 will be described with reference to FIG. 4. The light-receiving element 20 receives not only light transmitted from the light-emitting element 10 but also extraneous light (for example, sunlight and fluorescent light). The extraneous light does not become a pulsed signal and becomes a continuous signal on a time axis. In a case where light emitted from the light-emitting element 10 enters the light-receiving element 20 after being reflected by a part other than a blood vessel or directly enters the light-receiving element 20, the light becomes a noise component. A noise component derived from the light-emitting element 10 becomes a pulsed signal having the same cycle as a pulse wave signal. This noise is called stray light noise. A detection signal F(t) that has been received by the light-receiving element 20 and been amplified by the amplification unit 30 is represented by the following equation (1).

$$F(t)=fb(t)*fp(t)+Vb*fp(t)+Vdc \quad (1)$$

In this equation, fb(t) represents a pulse wave component, fp(t) represents a pulse function (a binary number of 0 or 1), Vb represents a noise component corresponding to stray light having no pulse wave component, and Vdc represents a noise component such as extraneous light.

The envelope extraction unit 40 extracts the envelope of the detection signal (see an output waveform at a node 30a in FIG. 3) amplified by the amplification unit 30 (see an output waveform at a node 40a in FIG. 3). The envelope extraction unit 40 therefore includes an envelope detection circuit including the diode 41, a resistor 42, and a capacitor 43. More specifically, a parallel circuit of the resistor 42 and the capacitor 43 is connected to the cathode terminal of the diode 41. The other end of the parallel circuit of the resistor 42 and the capacitor 43 is connected to the ground. The time constants of the resistor 42 and the capacitor 43 in the parallel circuit are set so that a pulsed high-frequency component is removed and the envelope of an input waveform is extracted in an output waveform.

More specifically, in the envelope extraction unit 40, the diode 41 performs half-wave rectification upon the intermittent pulsed detection signal (see the output waveform at the node 30a in FIG. 3) output from the amplification unit 30. The parallel circuit of the resistor 42 and the capacitor 43 extracts the envelope of the detection signal that has been subjected to the half-wave rectification (see the output waveform at the node 40a in FIG. 3). That is, as illustrated in FIG. 3, the envelope extraction unit 40 converts the pulsed detection signal into an analog signal whose peak value continuously varies along the envelope of its pulse train. The output terminal of the envelope extraction unit 40 is connected to the filter 50. An envelope signal extracted by the envelope extraction unit 40 is input into the filter 50.

The filter 50 removes a pulse wave component from the envelope signal (see the output waveform at the node 40a in FIG. 3) to obtain a baseline signal (see an output waveform at a node 50a in FIG. 3). That is, the filter 50 corresponds to a baseline signal acquisition unit. The pulse wave component has a frequency in the range of approximately 0.5 Hz to 3.3 Hz in a case where the number of pulses per minute is in the range of approximately 30 to 200. Examples of a method of removing this pulse wave component from an envelope signal in a detection signal include a method using a low-pass filter for selectively passing detection signals of less than 0.5 Hz. A low-frequency component that has passed through the low-pass filter is a noise component such as stray light or extraneous light obtained by the removal of a pulse wave component. The displacement of this noise component on a time axis is referred to as a baseline signal (baseline).

As the filter 50, a low-pass filter having the passband of less than 0.5 Hz can be used as described above. In the biosensor 1, the filter 50 is formed of a Sallen-Key second-order low-pass filter circuit that is a linear analog filter using an operational amplifier 51.

The output terminal of the filter 50 is connected to a first resistor 73 in the differential amplification circuit 70, and is connected to the input terminal (inverting input (−) terminal) of an operational amplifier 71 in the differential amplification circuit 70 via the first resistor 73. The baseline signal obtained by the filter 50 is output to the differential amplification circuit 70.

The adjustment unit 60, on the basis of the amplitude of the baseline signal (see an output waveform at the node 50a in FIG. 3), adjusts the amplitude of the detection signal (see the output waveform at the node 30a in FIG. 3) that is to be input into the differential amplification circuit 70 through the second path 82 (see the output waveform at a node 60a in FIG. 3). As illustrated in the output waveforms at the nodes 40a and 50a in FIG. 3, a constant loss (attenuation) from an original waveform represented by a broken line occurs in the baseline signal obtained on the first path 81 owing to signal processing performed by the envelope extraction unit 40 and the filter 50. Accordingly, in the biosensor 1, the amount of attenuation of a signal on the first path 81 is checked in advance. On the basis of the amount of attenuation, the adjustment unit 60 adjusts the gain of the differential amplification circuit 70 for a detection signal passing through the second path 82. That is, the amplitude of the baseline signal obtained on the first path 81 and the amplitude of a noise component in the detection signal adjusted on the second path 82 are matched for the differential amplification circuit 70.

More specifically, as the adjustment unit 60, the diode 61 having an internal resistance value corresponding to the amount of attenuation of the baseline signal on the first path 81 is disposed on the second path 82. The cathode terminal of the diode 61 is connected to a second resistor 74 forming the differential amplification circuit 70, and is connected to the input terminal (non-inverting input (+) terminal) of the operational amplifier 71 forming the differential amplification circuit 70 via the second resistor 74. That is, on the second path 82, the internal resistance value of the diode 61 is added to the resistance value of the second resistor 74 at the connection thereof to the input terminal (non-inverting input (+) terminal) of the operational amplifier 71. Accordingly, a gain for the detection signal to be input into the non-inverting input (+) terminal of the operational amplifier 71 through the second path 82 is reduced by the amount of attenuation of the baseline signal (see the output waveform at the node 60a in FIG. 3). In order to adjust a gain, the adjustment unit 60 may use any part having a resistance component with which the gain of the differential amplification circuit 70 can be adjusted, for example, a variable resistor, instead of the diode 61.

The differential amplification circuit 70 takes a difference between the detection signal (see the output waveform at the node 60a in FIG. 3) adjusted by the adjustment unit 60 on the second path 82 and the baseline signal (see the output waveform at the node 50a in FIG. 3) obtained by the filter 50 on the first path 81 and amplifies the difference (differential amplification) (see output waveforms at nodes 70 and 70a in FIG. 3). The differential amplification circuit 70 is therefore formed of a differential amplification circuit including the operational amplifier 71, the first resistor 73, the second resistor 74, and a feedback resistor 75.

More specifically, the operational amplifier 71 forming the differential amplification circuit 70 takes a difference between the adjusted detection signal input from the second resistor 74 into the non-inverting input (+) terminal and the baseline signal input from the first resistor 73 into the inverting input (−) terminal and amplifies the difference. As a result, a noise component in the detection signal is removed and a pulse wave component is amplified. The output terminal of the operational amplifier 71 is connected to the microcontroller 90. The amplified pulse wave component (photoplethysmographic signal) is output to the microcontroller 90.

The microcontroller 90 processes the photoplethysmographic signal (pulse wave component) obtained by the differential amplification performed by the differential amplification circuit 70 to obtain biological information such as information on a user's pulse. The microcontroller 90 outputs a driving signal to the light-emitting element 10. The microcontroller 90 therefore includes an analog-to-digital (A/D) converter 92 that is an input interface, a central processing unit (CPU) 95 for performing computation processing upon a detection signal input from the A/D converter 92, a Read-Only Memory (ROM) for storing a program that causes the CPU 95 to perform various pieces of processing and data, a Random Access Memory (RAM) for temporarily storing various pieces of data including a result of computation, and the output port 94 from which a driving signal is output. In the microcontroller 90, the CPU 95 executes a program stored in the ROM, so that the functions of a computation unit 96 and a driving signal generation unit 97 are achieved.

The A/D converter 92 converts the photoplethysmographic signal (pulse wave component) output from the differential amplification circuit 70 into digital data with a predetermined sampling period. The converted photoplethysmographic signal is output to the computation unit 96.

The computation unit 96 processes the input photoplethysmographic signal to obtain biological information such as pulse information. The obtained biological information such as pulse information is externally output or is stored in the above-described RAM.

The driving signal generation unit 97 generates a pulsed driving signal used to drive the light-emitting element 10 and outputs the generated driving signal from the output port 94. The setting of the driving signal generation unit 97 can be performed so that, for example, a pulse wave of approximately 600 Hz is generated as a driving signal.

In the biosensor 1 having the above-described configuration, the driving signal generation unit 97 in the microcontroller 90 generates, for example, a pulse signal of 600 Hz and outputs the generated pulse signal from the output port 94. Upon receiving the pulse signal, the light-emitting element 10 emits pulse light of a predetermined wavelength in accordance with the pulse signal. Pulse light that has been emitted from the light-emitting element 10 and passed through or been reflected by the human body 100 such as a fingertip enters the light-receiving element 20 and is converted into an electric signal by the light-receiving element 20 (a detection signal) (see the output waveform at the node 20a in FIG. 3). The detection signal converted by the light-receiving element 20 is subjected to current/voltage conversion and amplification in the amplification unit 30 (see the output waveform at the node 30a in FIG. 3).

The detection signal amplified by the amplification unit 30 branches off into the first path 81 and the second path 82 at the branch point 80. On the first path 81, the envelope extraction unit 40 extracts an envelope from the detection signal (see the output waveform at the node 40a in FIG. 3). That is, the envelope of the pulsed detection signal is extracted and an envelope signal with a continuous waveform is output.

The filter 50 removes an envelope signal of frequencies including a pulse wave component from the envelope signal extracted by the envelope extraction unit 40 to obtain a baseline signal (see the output waveform at the node 50a in FIG. 3). That is, the filter 50 selectively passes a detection signal of less than frequencies including a pulse wave component to obtain a baseline signal.

On the other hand, on the second path 82, the detection signal passes through the adjustment unit 60. As a result, on the basis of the amount of attenuation of the baseline signal obtained through the first path 81, the gain of the differential amplification circuit 70 for the detection signal adjusted on the second path 82 is adjusted (see the output waveform at the node 60a in FIG. 3).

The differential amplification circuit 70 takes a difference between the detection signal adjusted on the second path 82 and the baseline signal obtained through the first path 81 and amplifies the difference (differential amplification) (see the output waveform at the node 70a in FIG. 3). As a result, a noise component such as extraneous light superimposed on the adjusted detection signal is cut and a pulse wave component is obtained and is then amplified. The S/N ratio of the final photoplethysmographic signal (pulse wave component) is improved (see the output waveform at the node 70a in FIG. 3). In the biosensor 1, an operational amplifier for a single power supply is used. Accordingly, when the difference between the adjusted detection signal (see the output waveform at the node 60a in FIG. 3) and the baseline signal (see the output waveform at the node 50a in FIG. 3) is taken and a photoplethysmographic signal (pulse wave component) is output from the differential amplification circuit 70, an output between pulses in the photoplethysmographic signal does not become a negative value and becomes 0 V.

The photoplethysmographic signal (pulse wave component) that has been subjected to differential amplification in the differential amplification circuit 70 is input into the microcontroller 90. The photoplethysmographic signal input into the microcontroller 90 is transmitted to the computation unit 96 via the A/D converter 92. The computation unit 96 processes the photoplethysmographic signal to obtain, for example, biological information such as pulse information.

According to this embodiment, the envelope extraction unit 40 extracts an envelope from the detection signal that has been output from the light-receiving element 20 and amplified by the amplification unit 30. The filter 50 removes a pulse wave component from an envelope signal based on the envelope to obtain a baseline signal. The baseline signal can therefore varies in accordance with the change in a noise component superimposed on the detection signal which is caused by, for example, the change in the movement of a human body or the change in extraneous light. The differential amplification circuit 70 takes a difference between the detection signal adjusted on the second path 82 and the baseline signal obtained through the first path 81 and amplifies the difference. As a result, a noise component can be cut and a photoplethysmographic signal (pulse wave component) included in the detection signal can be obtained. Even in a case where a noise component such as extraneous light varies, the S/N ratio of a final photoplethysmographic signal can be improved.

Furthermore, according to this embodiment, the light-emitting element 10 flashes in response to a pulsed driving signal. As compared with a case where the light-emitting element 10 is kept lighted, power consumption can be reduced. The envelope extraction unit 40 converts a pulsed detection signal into an envelope signal with a continuous waveform representing an envelope (the envelope of the detection signal). The filter 50 removes a pulse wave component from the envelope signal to obtain a baseline signal with a continuous waveform. That is, since the baseline signal corresponds to a noise component obtained by the removal of the pulse wave component, the baseline signal varies in accordance with the change in the noise component. Since the differential amplification circuit 70 takes a difference between a pulsed detection signal and the baseline signal and amplifies the difference, a noise component is cut. Therefore, even in a case where a noise component such as extraneous light varies, the S/N ratio of a final photoplethysmographic signal can be improved.

Still furthermore, according to this embodiment, the filter 50 is formed of a Sallen-Key second-order low-pass filter using the operational amplifier 51. The Sallen-Key second-order low-pass filter removes a detection signal of frequencies including a pulse wave component from an envelope signal. More specifically, a detection signal of less than frequencies including a pulse wave component is selectively passed, so that a baseline signal is obtained. Since the baseline signal corresponds to a noise component obtained by the removal of a pulse wave component, the baseline signal varies in accordance with the change in the noise component. Accordingly, by taking a difference between the adjusted detection signal and the baseline signal, a noise component can be cut.

Still furthermore, according to this embodiment, on the basis of the amplitude of the baseline signal, the amplitude of a detection signal to be input into the differential amplification circuit 70 is adjusted. More specifically, the diode 61 having an internal resistance corresponding to the amount of attenuation of the amplitude of a baseline signal 50a obtained through the first path 81 is disposed on the second path 82. Therefore, the gain of the differential amplification circuit 70 for the detection signal passing through the second path 82 is adjusted (see the output waveform at the node 60a in FIG. 3). As a result, the amplitude of a noise component included in the detection signal adjusted through the second path 82 and the amplitude of the baseline signal obtained through the first path 81 are matched for the differential amplification circuit 70. By taking a difference between the adjusted detection signal and the baseline signal, it is therefore possible to efficiently cut a noise component and improve the S/N ratio of a final photoplethysmographic signal (pulse wave component).

Still furthermore, according to this embodiment, in order to cut a noise component such as extraneous light, there is no need to feed a reference voltage generated by a processor, which is a digital circuit, back to a current/voltage conversion circuit near a light-receiving element. The light-receiving section 5, the envelope extraction unit 40, the filter 50, and the differential amplification circuit 70 can be achieved with only an analog circuit. That is, the transmission of noise from a digital circuit probably does not occur. It is therefore possible to reduce noise transmitted from a digital circuit.

(Modification)

Figure 5:
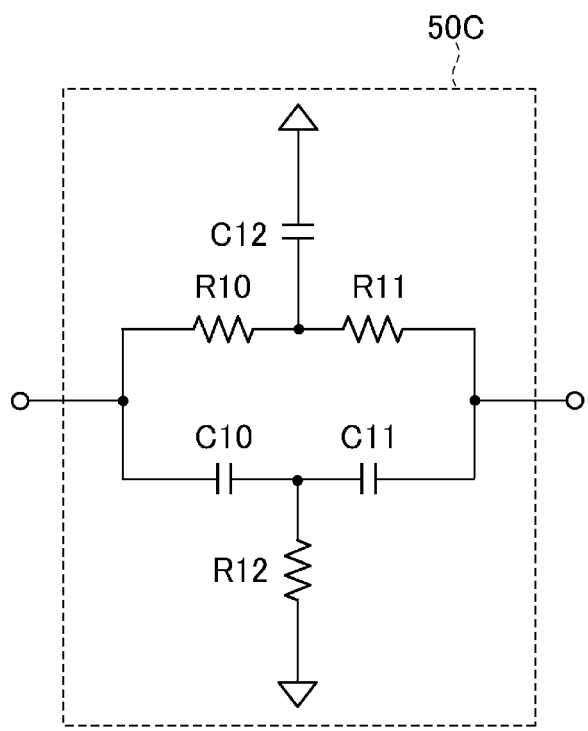
FIG. 5 is a circuit diagram of a band elimination filter in a biosensor that is a modification.

In the above-described first embodiment, a Sallen-Key second-order low-pass filter is used in the filter 50. However, for example, a band elimination filter 50C illustrated in FIG. 5 may be used. The band elimination filter 50C selectively blocks the passage of a signal in a frequency band (stop band) including a pulse wave component. That is, the band elimination filter 50C removes a pulse wave component from an envelope signal to obtain a baseline signal. In order to sufficiently remove a pulse wave component using the band elimination filter 50C, it is desirable that not only the fundamental frequency of a pulse wave component but also the harmonic of the pulse wave component be included in the stop band. Therefore, a band elimination filter may have a plurality of stages.

In this case, by setting a stop band to the range of approximately 0.5 Hz to 3.3 Hz when the frequency of a pulse wave component is in the range of approximately 0.5 Hz to 3.3 Hz, the band elimination filter 50C selectively blocks the passage of a signal in a frequency band (stop band) including the pulse wave component. As a result, a baseline signal can be obtained. Since the baseline signal corresponds to a noise component obtained by the removal of a pulse wave component, the baseline signal varies in accordance with the change in the noise component. Therefore, by taking a difference between the adjusted detection signal and the baseline signal, a noise component such as extraneous light can be cut.

In the above-described first embodiment, as the adjustment unit 60, the diode 61 having an internal resistance corresponding to the amount of attenuation of the amplitude of a baseline signal is disposed on the second path 82. However, an amplification circuit for amplifying the baseline signal by the amount of attenuation of the amplitude of the baseline signal may be disposed on the first path. That is, the amount of attenuation of a baseline signal on the first path is checked in advance, and the amplification circuit amplifies the baseline signal so that the baseline signal is compensated for the amount of attenuation. As a result, the amplitude of the baseline signal that has been amplified and compensated for the amount of attenuation on the first path and the amplitude of a noise component in the detection signal that has been amplified by the amplification unit 30 and passed through the second path can be matched for the differential amplification circuit 70. The differential amplification circuit 70 takes a difference between the amplified detection signal and the baseline signal that has been amplified and compensated for the amount of attenuation, so that a noise component can be efficiently cut and the S/N ratio of a photoplethysmographic signal (pulse wave component) can be further improved.

Second Embodiment

Figure 6:
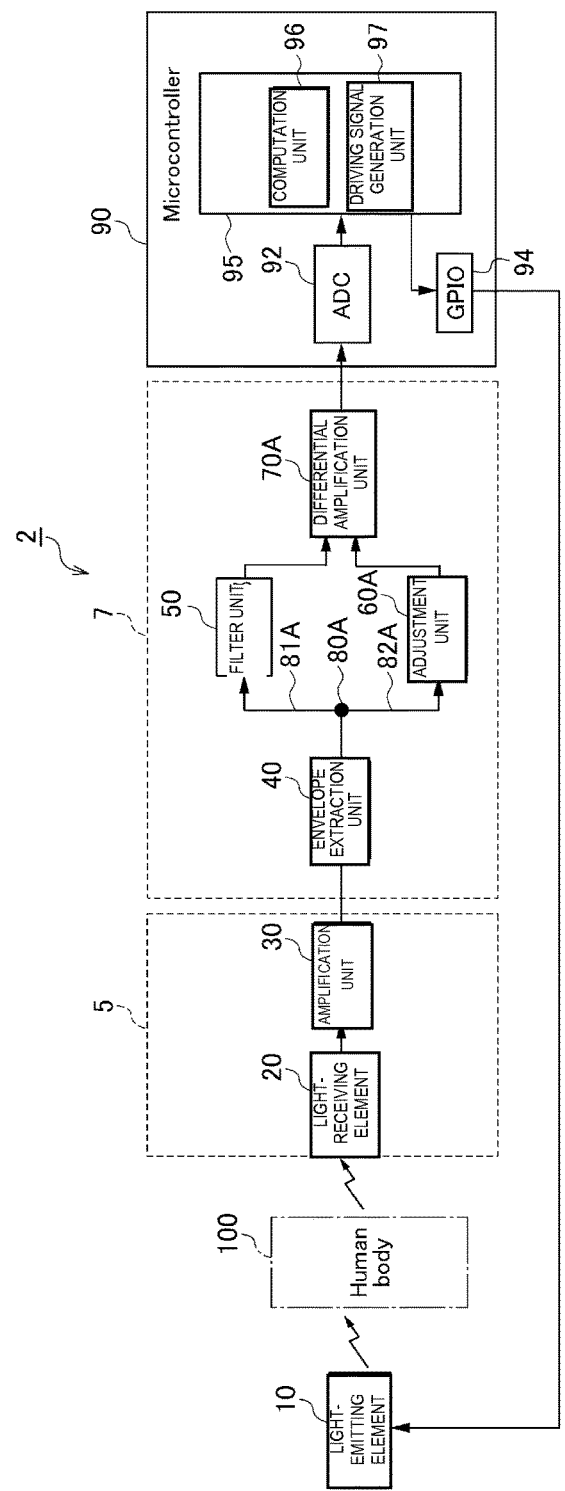
FIG. 6 is a block diagram illustrating the configuration of a biosensor according to a second embodiment.
Figure 7:
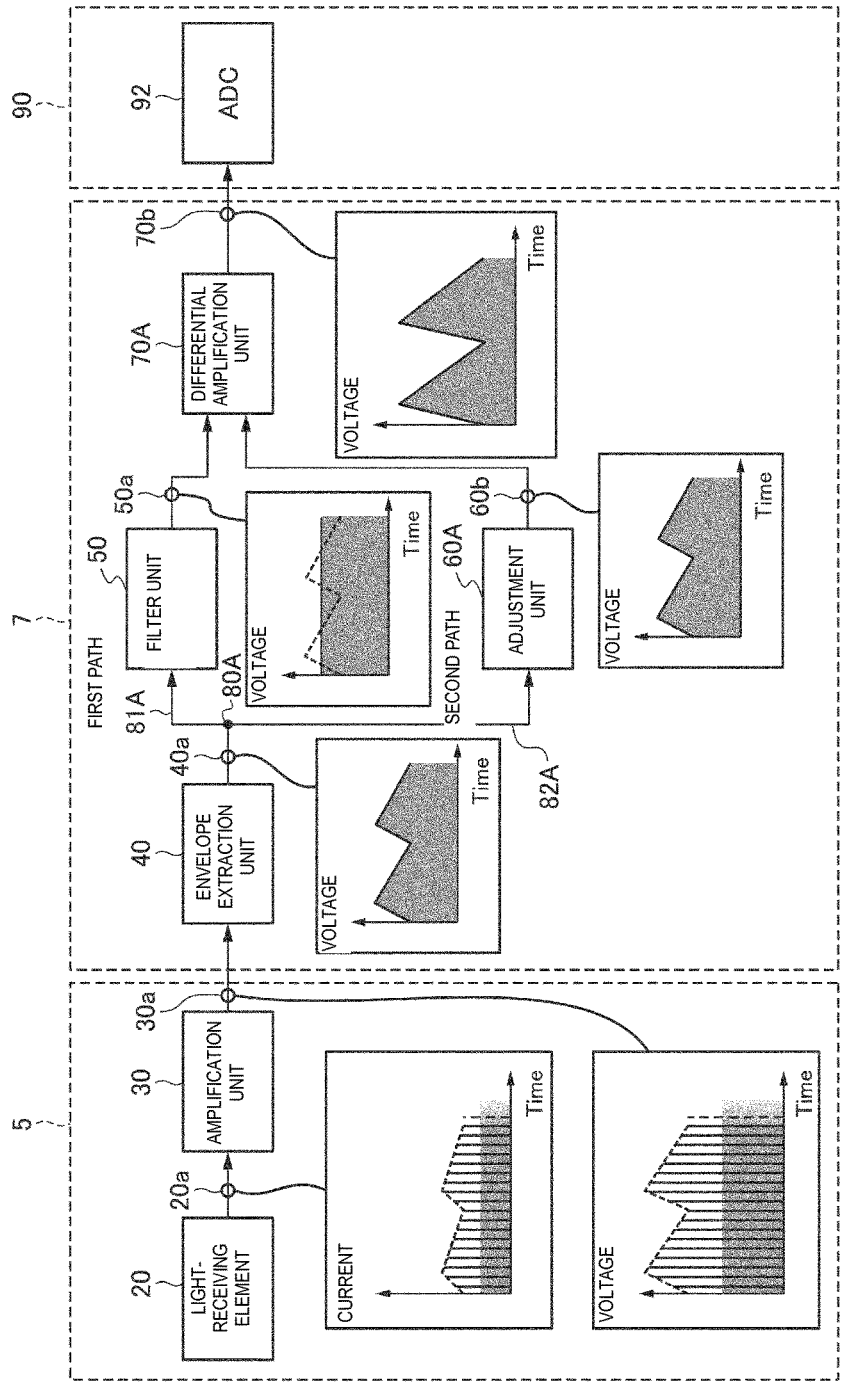
FIG. 7 is a diagram illustrating a signal waveform at each node in a biosensor according to the second embodiment.

Next, the configuration of a biosensor 2 according to the second embodiment will be described with reference to FIGS. 6 and 7. The difference between the biosensor 2 and the biosensor 1 according to the first embodiment will be mainly described, and the description of the same or similar configuration will be simplified or omitted. FIG. 6 is a block diagram illustrating the configuration of the biosensor 2 according to the second embodiment. FIG. 7 is a diagram illustrating a signal waveform at each node in the biosensor 2. Referring to FIGS. 6 and 7, the same reference numerals are used to identify parts already described in the first embodiment.

The biosensor 2 includes a pulse wave detection unit 7 instead of the pulse wave detection circuitry 6. In the pulse wave detection circuitry 6 in the biosensor 1, the output of the amplification unit 30 branches off into the first path 81 and the second path 82 at the branch point 80. However, in the pulse wave detection unit 7 in the biosensor 2, the output of the amplification unit 30 does not branch off and is input into the envelope extraction unit 40. The output of the envelope extraction unit 40 branches off into a first path 81A and a second path 82A at a branch point 80A. In addition to this branch point, the pulse wave detection unit 7 differs from the pulse wave detection circuitry 6 in that an adjustment unit 60A is provided instead of the adjustment unit 60 and a differential amplification circuit 70A is provided instead of the differential amplification circuit 70. On the first path 81A, the filter 50 removes a pulse wave component from an envelope signal (see the output waveform at the node 40a in FIG. 7) extracted by the envelope extraction unit 40 to obtain a baseline signal (see the output waveform at the node 50a in FIG. 7). On the second path 82A, the envelope signal (see the output waveform at the node 40a in FIG. 7) extracted by the envelope extraction unit 40 is input into the adjustment unit 60A. The other configuration is the same as or similar to that of the biosensor 1, and the detailed description thereof will be therefore omitted.

On the basis of the amplitude of the above-described baseline signal (see the output waveform at the node 50a in FIG. 7), the adjustment unit 60A adjusts the amplitude of an envelope signal (see the output waveform at the node 40a in FIG. 7) to be input into the differential amplification circuit 70A through the second path 82A (see an output waveform at a node 60b in FIG. 7). As illustrated in the output waveform at the node 50a in FIG. 7, a constant loss (attenuation) from an original waveform represented by a broken line occurs in the baseline signal obtained on the first path 81A owing to signal processing performed by the filter 50. Accordingly, in the biosensor 2, the amount of attenuation of a signal on the first path 81A is checked in advance. On the basis of the amount of attenuation, the adjustment unit 60A adjusts the gain of the differential amplification circuit 70A for an envelope signal passing through the second path 82A. As the adjustment unit 60A, any part having a resistance component with which the gain of the differential amplification circuit 70A can be adjusted, for example, a variable resistor, may be used. In the biosensor 2, in a case where the filter 50 has a small loss, the amplitude of the baseline signal and the amplitude of a noise component in the envelope signal are the same. Accordingly, the adjustment unit 60A can be omitted.

The differential amplification circuit 70A takes a difference between the envelope signal adjusted on the second path 82A and the baseline signal obtained on the first path 81A and amplifies the difference. Like the differential amplification circuit 70, the differential amplification circuit 70A is therefore formed of a differential amplification circuit including the operational amplifier 71, the first resistor 73, a second resistor 74, and the feedback resistor 75. The differential amplification circuit 70A corresponds to the difference acquisition unit. The pulse wave component (photoplethysmographic signal) that has been subjected to differential amplification in the differential amplification circuit 70A is input into the microcontroller 90.

In the biosensor 2 according to this embodiment, the driving signal generation unit 97 in the microcontroller 90 generates, for example, a pulse signal of 600 Hz and outputs the generated pulse signal from the output port 94. Upon receiving the pulse signal, the light-emitting element 10 emits pulse light of a predetermined wavelength in accordance with the pulse signal. The pulse light that has been emitted from the light-emitting element 10 and passed through or been reflected by the human body 100 such as a fingertip enters the light-receiving element 20 and is converted into an electric signal (a detection signal) by the light-receiving element 20 (see the output waveform at the node 20a in FIG. 7). The detection signal converted by the light-receiving element 20 is subjected to current/voltage conversion and amplification in the amplification unit 30 (see the output waveform at the node 30a in FIG. 7).

The envelope extraction unit 40 extracts an envelope from the detection signal amplified by the amplification unit 30. That is, the envelope of the pulsed detection signal (see the output waveform at the node 30a in FIG. 7) is extracted and an envelope signal with a continuous waveform (see the output waveform at the node 40a in FIG. 7) is output.

The output of the envelope signal extracted ty the envelope extraction unit 40 branches off into the first path 81A and the second path 82A at the branch point 80A. On the first path 81A, the filter 50 removes the above-described pulse wave component to obtain a baseline signal (see the output waveform at the node 50a in FIG. 7).

On the second path 82A, the envelope signal passes through the adjustment unit 60A. As a result, on the basis of the amount of attenuation of the baseline signal obtained on the first path 81A, the gain of the differential amplification circuit 70A for the envelope signal that has passed through the second path 82A is adjusted (see the output waveform at the node 60b in FIG. 7).

The differential amplification circuit 70A takes a difference between the envelope signal adjusted on the second path 82A and the baseline signal obtained through the first path 81A and amplifies the difference (differential amplification) (see an output waveform at a node 70b in FIG. 7). As a result, a noise component such as extraneous light superimposed on the adjusted envelope signal is cut and a pulse wave component is amplified. The S/N ratio of the final amplified photoplethysmographic signal (pulse wave component) is improved (see the output waveform at the node 70b in FIG. 7). In the biosensor 1, the photoplethysmographic signal output from the differential amplification circuit 70 is a pulsed signal (see the output waveform at the node 70a in FIG. 3). On the other hand, in the biosensor 2, the photoplethysmographic signal output from the differential amplification circuit 70A is a signal with a continuous waveform (see the output waveform at the node 70b in FIG. 7).

The pulse wave component (photoplethysmographic signal) obtained by the differential amplification circuit 70A is input into the microcontroller 90. The photoplethysmographic signal input into the microcontroller 90 is transmitted to the computation unit 96 via the A/D converter 92. The computation unit 96 processes the photoplethysmographic signal to obtain, for example, biological information such as pulse information.

According to this embodiment, the light-emitting element 10 flashes in response to the above-described pulsed driving signal. As compared with a case where the light-emitting element 10 is kept lighted, power consumption can be reduced. The envelope of the amplified detection signal is extracted, so that the pulsed detection signal is converted into an envelope signal with a continuous waveform representing an envelope (the envelope of the detection signal) (see the output waveform at the node 40a in FIG. 7). A pulse wave component is removed from the envelope signal, so that a baseline signal with a continuous wave (see the output waveform at the node 50a in FIG. 7) is obtained. A difference between the envelope signal with a continuous waveform for which a gain has been adjusted (see the output waveform at the node 60b in FIG. 7) and the baseline signal is taken and is then amplified, so that a noise component such as extraneous light is cut and a photoplethysmographic signal (pulse wave component) included in the adjusted envelope signal is obtained (see the output waveform at the node 70b in FIG. 7). Accordingly, even in a case where a noise component such as extraneous light varies, the S/N ratio of a final photoplethysmographic signal can be improved.

Third Embodiment

Figure 8:
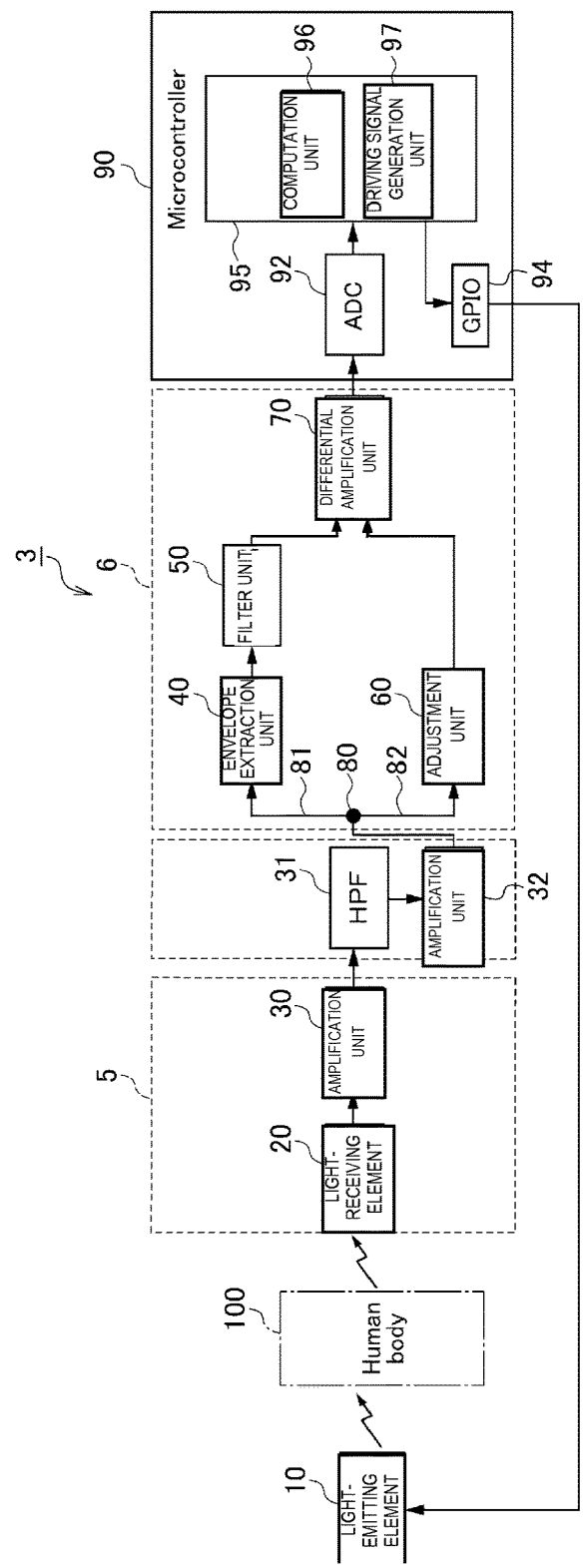
FIG. 8 is a block diagram illustrating the configuration of a biosensor according to a third embodiment.
Figure 9:
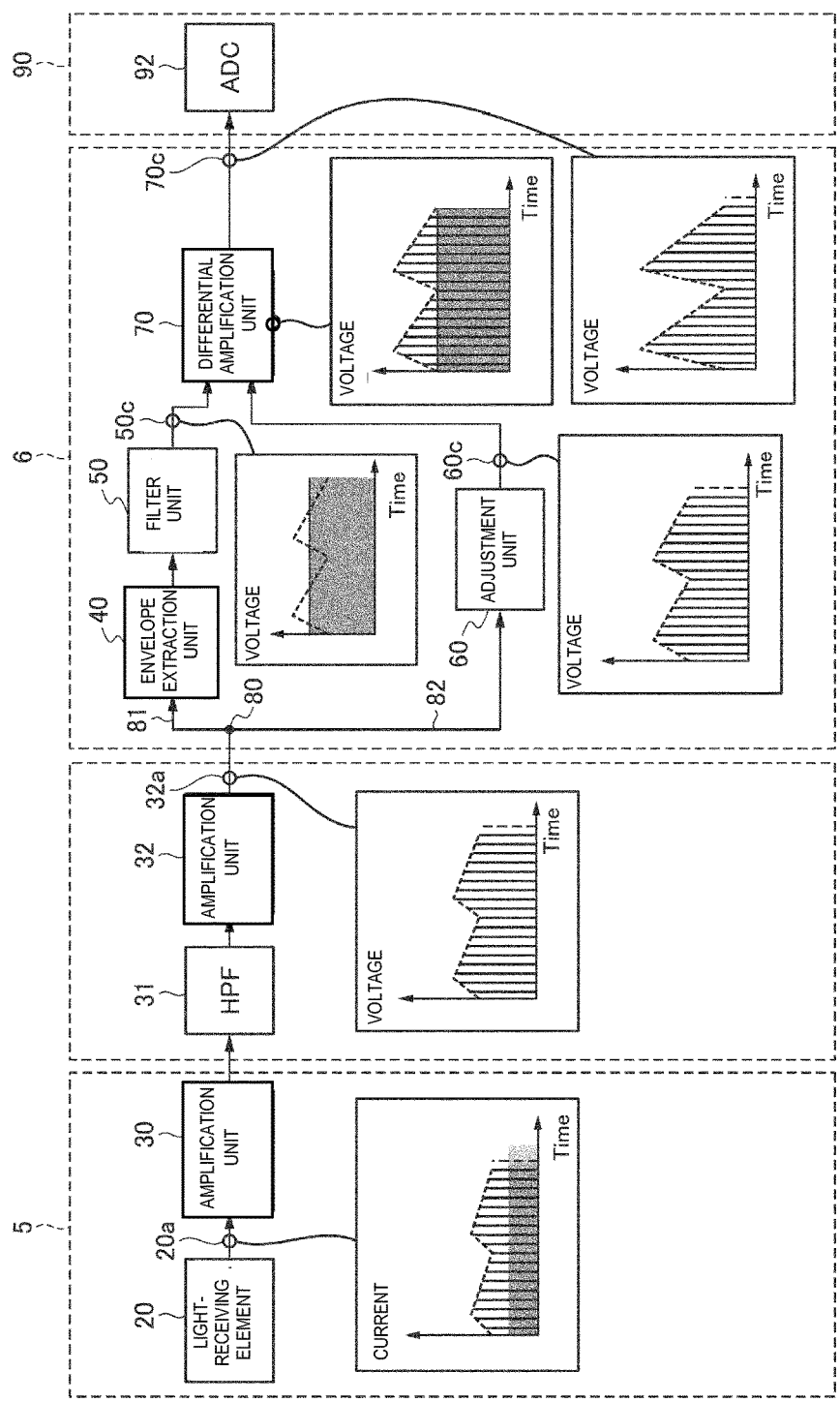
FIG. 9 is a diagram illustrating a signal waveform at each node in a biosensor according to the third embodiment.

Next, the configuration of a biosensor 3 according to the third embodiment will be described with reference to FIGS. 8 and 9. The difference between the biosensor 3 and the biosensor 1 according to the first embodiment will be mainly described, and the description of the same or similar configuration will be simplified or omitted. FIG. 8 is a block diagram illustrating the configuration of the biosensor 3. FIG. 9 is a diagram illustrating a signal waveform at each node in the biosensor 3. Referring to FIGS. 8 and 9, the same reference numerals are used to identify parts already described in the first embodiment.

The biosensor 3 differs from the biosensor 1 in that the biosensor 3 further includes a high-pass filter 31 for, among detection signals that have been transmitted from the light-receiving element 20 and been subjected to initial-stage amplification in the amplification unit 30, selectively passing detection signals of frequencies equal to or higher than a predetermined frequency which include a pulse wave component and an amplification unit 32 for performing second-stage amplification upon the detection signal that has passed through the high-pass filter 31. The other configuration is the same as or similar to that of the biosensor 1, and the detailed description thereof will be omitted.

The high-pass filter 31 selectively passing detection signals of frequencies equal to or higher than a predetermined frequency which include a pulse wave component among amplified detection signals. That is, the high-pass filter 31 removes a low-frequency component such as a direct-current component including no pulse wave component from an amplified detection signal. That is, the S/N ratio of a detection signal that has passed through the high-pass filter 31 (hereinafter also referred to as "passed detection signal") is improved. For example, the high-pass filter 31 can be formed by connecting the amplification unit 30 and the amplification unit 32 with a capacitor disposed therebetween (alternating connection).

The amplification unit 32 amplifies the passed detection signal (see an output waveform at the node 32a in FIG. 9). The output of the amplification unit 32 branches of into the first path 81 and the second path 82 at the branch point 80. The output terminal of the amplification unit 32, which branches off at the branch point 80, is connected to the envelope extraction unit 40 on the first path 81 and the adjustment unit 60 on the second path 82. That is, the passed detection signal amplified by the amplification unit 32 is output to the envelope extraction unit 40 and the adjustment unit 60. As the amplification unit 32, a noninverting amplification circuit including an operational amplifier can be used.

Using the above-described configuration, in the biosensor 3 according to this embodiment, the envelope extraction unit 40 extracts the envelope of the passed detection signal (see the output waveform at the node 32a in FIG. 9). The filter 50 removes a pulse wave component from an envelope signal to obtain a baseline signal (see an output waveform at a node 50c in FIG. 9).

On the other hand, on the second path 82, the passed detection signal (see the output waveform at the node 32a in FIG. 9) passes through the adjustment unit 60 (see an output waveform at a node 60c in FIG. 9). The gain of the differential amplification circuit 70 for the passed detection signal that has passed through the second path 82 is adjusted in accordance with the amount of attenuation of the baseline signal obtained through the first path 81.

The differential amplification circuit 70 takes a difference between the passed detection signal adjusted on the second path 82 (see the output waveform at the node 60c in FIG. 9) and the baseline signal obtained through the first path 81 (see the output waveform at the node 50c in FIG. 9) and amplifies the difference (differential amplification) (see an output waveform at the node 70c in FIG. 9). As a result, a noise component such as extraneous light superimposed on the passed detection signal is cut and a pulse wave component is obtained. The S/N ratio of the final photoplethysmographic signal (pulse wave component) is improved.

According to this embodiment, the high-pass filter 31 can selectively pass detection signals of frequencies equal to or higher than a predetermined frequency which include a pulse wave component among detection signals that have been transmitted from the light-receiving element 20 and been amplified by the amplification unit 30. That is, the high-pass filter 31 removes a noise component that is less variable than a pulse wave component on a time axis. As a result, the S/N ratio of a passed detection signal that has passed through the high-pass filter 31 can be improved. Since the S/N ratio of a passed detection signal is improved, the amplification factor of the amplification unit 32 at the subsequent stage can be increased. It is therefore possible to prevent the saturation of a detection signal caused by, for example, a noise component such as extraneous light.

Furthermore, according to this embodiment, since the passed detection signal (see the output waveform at the node 60c in FIG. 9) adjusted on the second path 82 and the baseline signal (see the output waveform at the node 50c in FIG. 9) obtained through the first path 81 are originated from the passed detection signal that has passed through the high-pass filter 31, the S/N ratios of both of these signals can be improved. By taking a difference between these signals having the improved S/N ratios and amplifying the difference (see the output waveform at the node 70c in FIG. 9), a noise component can be more accurately cut.

Fourth Embodiment

Figure 10:
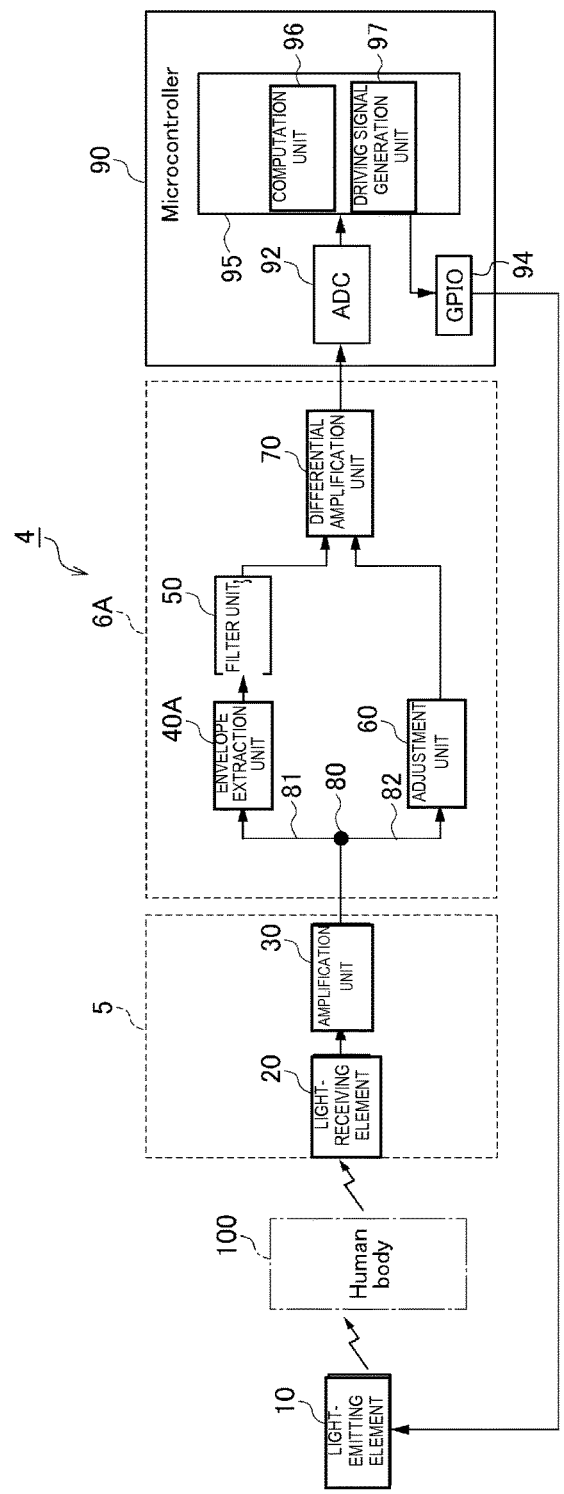
FIG. 10 is a block diagram illustrating the configuration of a biosensor according to a fourth embodiment.
Figure 11:
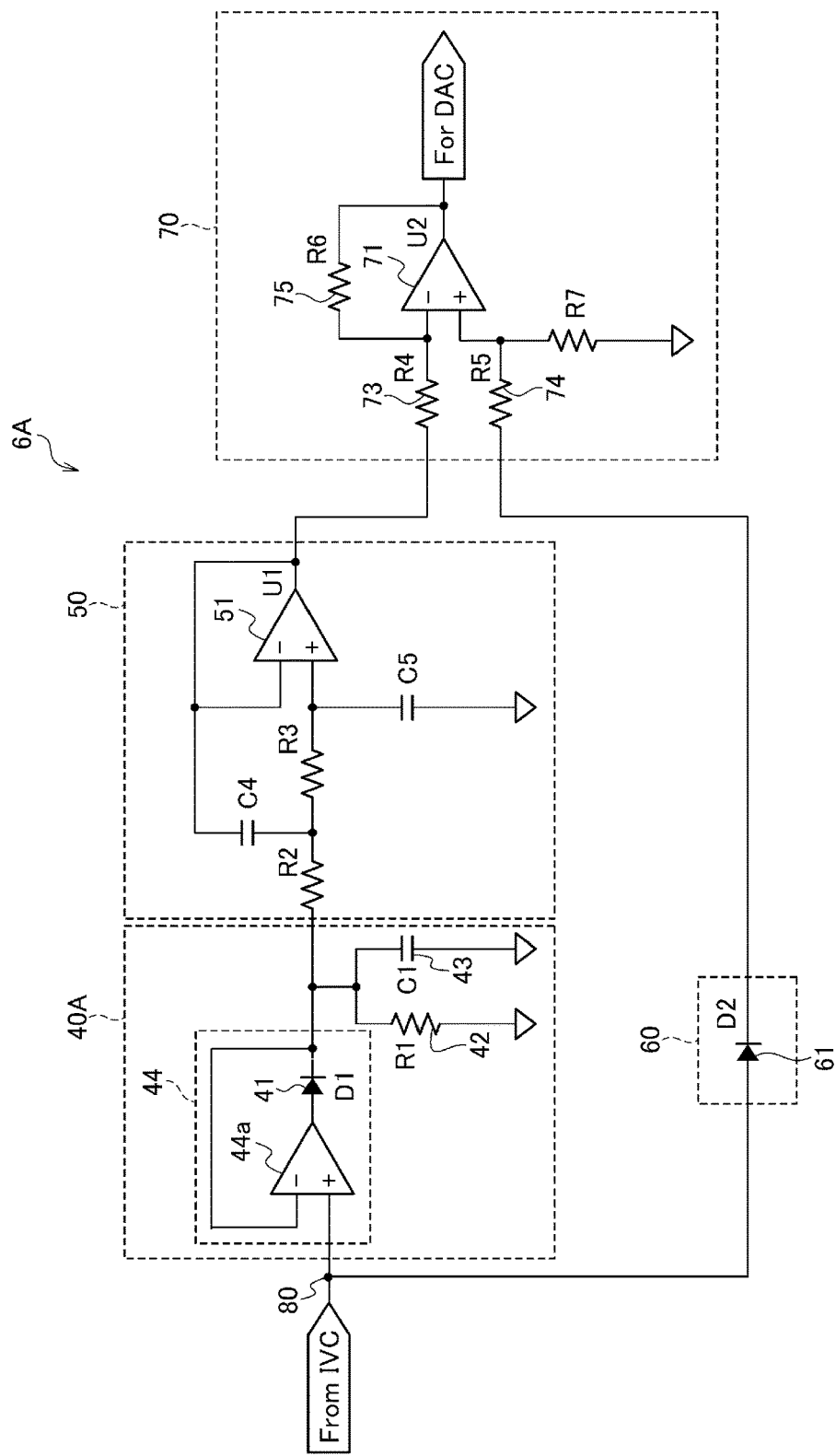
FIG. 11 is a circuit diagram of a pulse wave detection unit (envelope extraction unit) in a biosensor according to the fourth embodiment.
Figure 12:
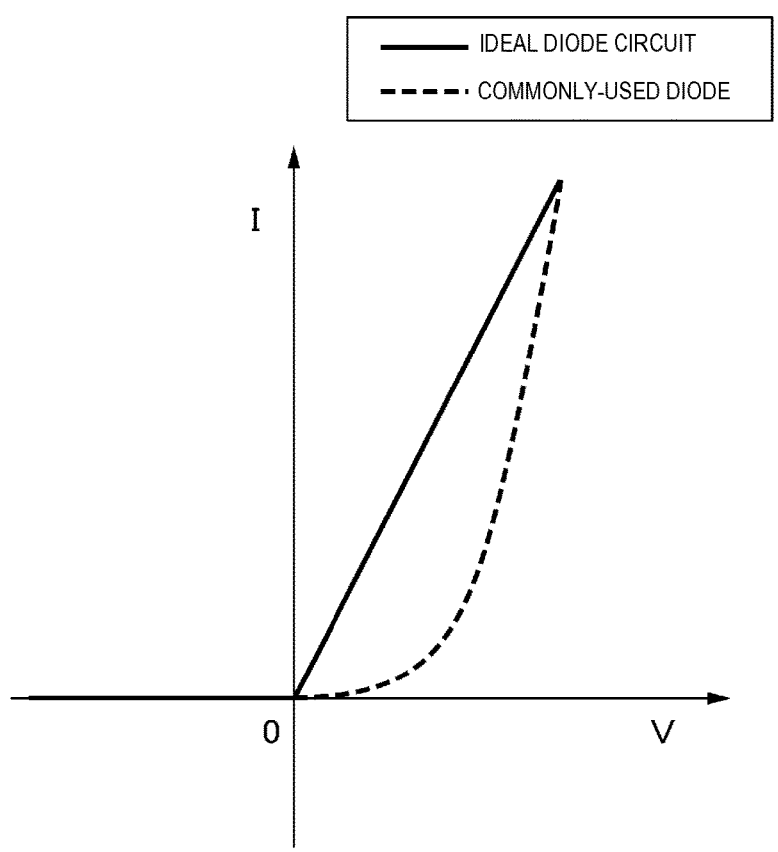
FIG. 12 is a diagram illustrating the V-I characteristics of an ideal diode circuit.

Next, the configuration of a biosensor 4 according to the fourth embodiment will be described with reference to FIGS. 10, 11, and 12. The difference between the biosensor 4 and the biosensor 1 according to the first embodiment will be mainly described, and the description of the same or similar configuration will be simplified or omitted. FIG. 10 is a block diagram illustrating the configuration of the biosensor 4 according to the fourth embodiment. FIG. 11 is a circuit diagram of a pulse wave detection unit 6A (envelope extraction unit 40A) forming the biosensor 4. FIG. 12 is a diagram illustrating the V-I characteristics of an ideal diode circuit 44 forming the envelope extraction unit 40A. Referring to FIGS. 10 and 11, the same reference numerals are used to identify parts already described in the first embodiment.

The biosensor 4 differs from the biosensor 1 in that the biosensor 4 includes the pulse wave detection unit 6A instead of the pulse wave detection circuitry 6. The pulse wave detection unit 6A differs from the pulse wave detection circuitry 6 in that the pulse wave detection unit 6A includes the envelope extraction unit 40A instead of the envelope extraction unit 40. The other configuration is the same as or similar to that of the biosensor 1, and the detailed description thereof will be therefore omitted.

The envelope extraction unit 40A extracts the envelope of the detection signal amplified by the amplification unit 30. The envelope extraction unit 40A therefore includes an envelope detection circuit including the ideal diode circuit 44, the resistor 42, and the capacitor 43. More specifically, the envelope extraction unit 40A includes the ideal diode circuit 44 for equivalently eliminating the forward voltage drop of the diode 41 (that is, eliminating the nonlinearity of the diode 41). The parallel circuit of the resistor 42 and the capacitor 43 is connected to the output of the ideal diode circuit 44. The other end of the parallel circuit of the resistor 42 and the capacitor 43 is connected to the ground.

The ideal diode circuit 44 includes an operational amplifier (differential amplifier) 44a having a non-inverting input (+) terminal for receiving a detection signal amplified by the amplification unit 30 connected thereto and the diode 41 having an anode terminal connected to the output terminal of the operational amplifier 44a and a cathode terminal connected to the output of the ideal diode circuit and the negative feedback loop (inverting input (−) terminal) of the operational amplifier 44a.

In the envelope extraction unit 40A, an intermittent pulsed detection signal output from the amplification unit 30 is subjected to half-wave rectification in the ideal diode circuit 44. From the detection signal that has been subjected to half-wave rectification, the parallel circuit of the resistor 42 and the capacitor 43 removes a high-frequency component to extract the envelope of the detection signal.

That is, the envelope extraction unit 40A converts the pulsed detection signal into an analog signal whose peak value continuously varies along the envelope of its pulse train. The output terminal of the envelope extraction unit 40A is connected to the filter 50. An envelope signal extracted by the envelope extraction unit 40A is input into the filter 50.

In a case where the detection of an envelope of a detection signal (rectification) is performed with a commonly-used diode, the output of an envelope (the waveform of a pulse wave) is distorted under the influence of the nonlinearity of the diode represented by a broken line in FIG. 12. Since the forward voltage temperature characteristics of a diode is not generally so good (approximately −2 mV/° C.), temperature characteristics at the time of the detection of an envelope is deteriorated. On the other hand, in the ideal diode circuit 44 in which the diode 41 is disposed in the negative feedback part of the operational amplifier 44a, the nonlinearity and temperature characteristics of the diode 41 are compressed to a fraction of the loop gain of the operational amplifier 44a. Accordingly, as represented by a solid line in FIG. 12, ideal V-I characteristics showing a linear operation in the range of actual use can be achieved. The distortion of a pulse wave component and temperature characteristics, which become problems in commonly-used diodes, are improved.

As described above, the output terminal of the envelope extraction unit 40A is connected to the filter 50. An envelope signal extracted by the envelope extraction unit 40A is input into the filter 50. The description of the filter 50 has already been made and will be therefore omitted.

According to this embodiment, since the ideal diode circuit 44 for equivalently eliminating a forward voltage drop at the diode 41 is used, the nonlinearity of the commonly-used diode 41 does not become a problem and the distortion of the output of an envelope (the distortion of the waveform of a pulse wave) can be prevented.

Furthermore, according to this embodiment, since the diode 41 is disposed in the negative feedback part of the operational amplifier 44a, the nonlinearity and temperature characteristics of the diode 41 can be compressed to a fraction of the loop gain (can be improved). Thus, the ideal diode circuit 44 can be provided.

Embodiments of the present invention have been described. The present invention is not limited to these embodiments, and various changes can be made to these embodiments. For example, in the above-described embodiments, single-stage amplification is performed with the amplification unit 30 or two-stage amplification is performed with the amplification units 30 and 32. However, a three- or higher-order operational amplifier may be used.

In the above-described embodiments, the light-emitting element 10 emits pulse light in response to a pulsed driving signal and a pulse wave component is obtained from a pulsed detection signal output from the light-receiving element 20. However, the light-emitting element 10 may emit continuous light in response to a driving signal with a continuous waveform and a pulse wave component may be obtained from a detection signal with a continuous waveform output from the light-receiving element 20. In this case, the envelope extraction unit 40 can be omitted.

In the above-described embodiments, as the filter 50, a Sallen-Key second-order low-pass filter using the operational amplifier 51 is used. However, any low-pass filter capable of selectively passing a detection signal of a frequency lower than frequencies including a pulse wave component may be used. For example, a first-order low-pass filter including a resistor and a capacitor having the other end connected to the ground can be used. In this case, since an operational amplifier is not used, cost reduction can be achieved.

In the above-described embodiments, the microcontroller 90 processes a photoplethysmographic signal (pulse wave component) output from the differential amplification circuit 70 to obtain biological information such as information on user's pulse. However, the destination of a signal output from the differential amplification circuit 70 is not limited to the microcontroller 90 or an A/D converter, and may be, for example, another processing circuit, an analog meter, or a luminescent device.

In the above-described fourth embodiment, the ideal diode circuit 44 is applied to the biosensor 1 (the envelope extraction unit 40) according to the first embodiment. However, the ideal diode circuit 44 may be applied to the biosensor 2 according to the second embodiment or the biosensor 3 according to the third embodiment. In a case where the ideal diode circuit 44 is applied to the biosensor 2 according to the second embodiment, the ideal diode circuit (operational amplifier) may have an amplification function.

REFERENCE SIGNS LIST 1, 2, 3, and 4 biosensor
5 light-receiving section
6, 6A, and 7 pulse wave detection section
10 light-emitting element
20 light-receiving element
30 amplification unit
31 high-pass filter
40 and 40A envelope extraction unit
41 diode
44 ideal diode circuit
44a operational amplifier 50 filter unit (low-pass filter)
50C band elimination filter
60 and 60A adjustment unit
61 diode
70 and 70A differential amplification unit
80 and 80A branch point
81 and 81A first path
82 and 82A second path
90 microcontroller
92 A/D converter
94 output port
95 CPU
96 computation unit
97 driving signal generation unit

The invention claimed is:

1. A biosensor comprising:
a light-emitting element configured to emit light in response to a pulsed driving signal;
a light-receiving element configured to output a detection signal based on an intensity of light received;
an envelope extraction unit that includes an ideal diode circuit configured to equivalently eliminate a diode forward voltage drop, wherein the envelope extraction unit is configured to:
rectify the detection signal output from the light-receiving element using the ideal diode circuit,
remove a high-frequency component from the rectified detection signal, and
extract an envelope of the rectified detection signal;
a filter configured to remove a pulse wave component from the extracted envelope of the detection signal to generate a baseline signal; and
a difference acquisition circuit configured to amplify a difference between the detection signal and the baseline signal to generate an amplified pulse wave component including biological information.

2. The biosensor according to claim 1, further comprising a high-pass filter coupled between the light-receiving element and the envelope extraction unit and configured to selectively pass detection signals of frequencies equal to or higher than a predetermined frequency, including the pulse wave component to the envelope extraction unit.

3. The biosensor according to claim 1, wherein the ideal diode circuit includes an operational amplifier configured to receive the detection signal from the light-receiving element and a diode having an anode terminal connected to an output terminal of the operational amplifier and a cathode terminal connected to an output of the ideal diode circuit and a feedback loop of the operational amplifier.

4. The biosensor according to claim 1, wherein the filter is a band elimination filter configured to selectively block passage of the detection signal, among a plurality of detection signals, in a frequency band including a pulse wave component to acquire a baseline signal.

5. The biosensor according to claim 1, wherein the filter is a low-pass filter configured to selectively pass a detection signal, among a plurality of detection signals, of a frequency lower than frequencies including a pulse wave component to acquire a baseline signal.

6. The biosensor according to claim 1, further comprising an amplitude adjustment unit configured to adjust an amplitude of a signal to be input into the difference acquisition circuit based on an amplitude of the baseline signal generated by the filter.

7. The biosensor according to claim 1, wherein the envelope extraction unit includes a diode with an input coupled to the light-receiving element to receive the detection signal, and a resistive element and capacitive element each coupled to the output of the diode and ground.

8. The biosensor according to claim 7, wherein the filter includes an operational amplifier with an inverting input coupled to an output of the operational amplifier and a non-inverting input coupled to the output of the envelope extraction unit.

9. The biosensor according to claim 8, wherein the filter further includes a pair of resistive elements coupled in series between the non-inverting input and the output of the envelope extraction unit, a first capacitive element coupled to a node between the pair of resistive elements and the inverting input, and a second capacitive element coupled between the non-inverting input and ground.

10. The biosensor according to claim 9, wherein the difference acquisition circuit includes an operational amplifier with a non-inverting input coupled to an output of a diode, the diode having an input coupled to the light-receiving element to receive the detection signal, and
an inverting input coupled to the output of the filter.

11. The biosensor according to claim 10, wherein the diode comprises an internal resistance value corresponding to an amount of attenuation of the baseline signal.

12. The biosensor according to claim 1, further comprising a microcontroller having an A/D converter configured to convert the amplified pulse wave component into digital data with a predetermined sampling period.

13. The biosensor according to claim 12, wherein the microcontroller includes a computation unit configured to process the digital data to obtain the biological information.

14. A method for detecting biological information, the method comprising:
emitting light by a light-emitting element in response to a pulsed driving signal;
detecting light by a light-receiving element;
outputting, by the light-receiving element, a detection signal based on an intensity of the detected light;
rectifying, by an envelope extraction unit including an ideal diode circuit for equivalently eliminating a diode forward voltage drop, the detection signal output from the light-receiving element;
removing, by the envelope extraction unit, a high-frequency component from the rectified detection signal;
extracting, by the envelope extraction unit, an envelope of the rectified detection signal;
filtering the extracted envelope of the detection signal to remove a pulse wave component to generate a baseline signal; and
amplifying, by a difference acquisition circuit, a difference between the detection signal and the baseline signal to generate an amplified pulse wave component including biological information.

15. The method according to claim 14, further comprising filtering, by a high-pass filter, detection signals of frequencies equal to or higher than a predetermined frequency, including the pulse wave component.

16. The method according to claim 14, further comprising a converting, by an A/D converter, the amplified pulse wave component into digital data with a predetermined sampling period.

17. The method according to claim 16, further comprising, processing, by a computation unit, the digital data to obtain the biological information.

* * * * *